(12) United States Patent
Schneider et al.

(10) Patent No.: US 9,040,587 B2
(45) Date of Patent: *May 26, 2015

(54) HALO ACTIVE AROMATIC SULFONAMIDE ORGANIC COMPOUNDS AND USES THEREFOR

(76) Inventors: David J. Schneider, Union, KY (US); Charles A. Schneider, Villa Hills, KY (US)

(*) Notice: Subject to any disclaimer, the term of this patent is extended or adjusted under 35 U.S.C. 154(b) by 673 days.

This patent is subject to a terminal disclaimer.

(21) Appl. No.: 13/168,012

(22) Filed: Jun. 24, 2011

(65) Prior Publication Data

US 2011/0251284 A1  Oct. 13, 2011

Related U.S. Application Data

(63) Continuation-in-part of application No. 12/607,188, filed on Oct. 28, 2009, now Pat. No. 8,003,823, which is a continuation of application No. 11/216,495, filed on Aug. 31, 2005, now Pat. No. 7,629,492, which is a continuation-in-part of application No. 10/369,175, filed on Feb. 18, 2003, now Pat. No. 7,465,829.

(60) Provisional application No. 60/357,265, filed on Feb. 19, 2002.

(51) Int. Cl.
| | |
|---|---|
| *A61K 31/18* | (2006.01) |
| *C07C 311/30* | (2006.01) |
| *C07C 311/41* | (2006.01) |
| *C07C 303/00* | (2006.01) |
| *A01N 41/06* | (2006.01) |
| *C07C 311/00* | (2006.01) |
| *A01N 59/00* | (2006.01) |
| *A61K 31/63* | (2006.01) |

(52) U.S. Cl.
CPC .............. *A01N 41/06* (2013.01); *C07C 303/00* (2013.01); *C07C 311/00* (2013.01); *A01N 59/00* (2013.01); *A61K 31/18* (2013.01); *A61K 31/63* (2013.01)

(58) Field of Classification Search
CPC ...... C07C 311/12; C07C 311/48; A61K 31/18
USPC ......... 564/84, 90, 99; 558/413, 913; 514/602, 514/603, 604
See application file for complete search history.

(56) References Cited

U.S. PATENT DOCUMENTS

| | | | |
|---|---|---|---|
| 2,809,937 | A | 10/1957 | Gray |
| 6,296,841 | B1 | 10/2001 | Schneider |
| 7,465,823 | B2 | 12/2008 | Bhaskaran et al. |
| 7,465,829 | B2 | 12/2008 | Schneider et al. |
| 7,629,492 | B2 | 12/2009 | Schneider et al. |

FOREIGN PATENT DOCUMENTS

JP          10-81610          3/1998

OTHER PUBLICATIONS

FDA, Dry Milk Ordinance Supplement 1 Appendix B, pp. 87-88 (1995).
Mullen, The Biocides Business: Regulation, Safety and Applications, pp. 251-266 (2002).
Dawson et al., Inter. Assoc. Fish & Wildlife, Approval of Drugs for Public Fish Production, Second Mid-Year Report of Progress, pp. 1-11, (1996).
Chrzaszewska et al., PL 52046 (CA 69:18848 Best Available, Abstract), (1968).
International Search Report, mailed Apr. 18, 2007.
Chrzaszewska et al., PL 52046 (CA 69: 18848 Best Available, Abstract), (1968).

*Primary Examiner* — Andrew D Kosar
*Assistant Examiner* — Raymond Covington
(74) *Attorney, Agent, or Firm* — Richard M. Klein; Fay Sharpe LLP

(57) ABSTRACT

Aromatic N-halosulfonamide organic compounds have been known for over one hundred years. The ability of these compounds to release active halogen ions has been utilized in a range of biocidal and fungicidal applications. This disclosure deals with the use of halo active aromatic sulfonamide organic compounds as odor control and/or biocidal agents in a cleaning solution for use with bovines and other dairy animals.

16 Claims, No Drawings

HALO ACTIVE AROMATIC SULFONAMIDE ORGANIC COMPOUNDS AND USES THEREFOR

CROSS-REFERENCE TO RELATED APPLICATIONS

This application is a continuation-in-part of U.S. patent application Ser. No. 12/607,188, filed Oct. 28, 2009, now U.S. Pat. No. 8,003,823, which is a continuation of U.S. patent application Ser. No. 11/216,495, filed Aug. 31, 2005, now U.S. Pat. No. 7,629,492, which is a continuation-in-part of U.S. patent application Ser. No. 10/369,175, filed Feb. 18, 2003, now U.S. Pat. No. 7,465,829, which claims priority to U.S. Provisional Patent Application Ser. No. 60/357,265, filed Feb. 19, 2002, each of which is hereby incorporated herein by reference in its entirety.

BACKGROUND OF THE DISCLOSURE

This disclosure relates to particular uses for halo active aromatic sulfonamide organic compounds which have enhanced properties and minimal side effects as compared to the compounds of the prior art. In a broad context this disclosure relates to the use of halo active sulfonamide compounds for use in odor control and/or as a cleaning, disinfecting, and germicidal sanitizing agent for livestock and associated equipment.

When the halo active aromatic sulfonamide compounds set forth in this disclosure are used as a biocide, fungicide, odor control agent, or as a teat cleanser, solutions of the sulfonamide compound are brought into contact with the surface being treated. This contact is usually affected by spraying, washing, dipping, and/or mixing in such a manner as to contact the effected surface or substrate with an aqueous formulation of the desired sulfonamide compound or a blended mixture of same. This process is specifically effective in treating bovine/dairy animals and related milking equipment for mastitis, but is not particularly limited thereto.

Mastitis is a persistent, inflammatory reaction of the udder tissue in cows. This potentially fatal mammary gland infection is the most common disease in dairy cattle in the United States, and the costs to the dairy industry of mastitis are calculated to be in the billions of dollars annually.

Mastitis can cause a decline in potassium and lactoferrin. It also results in decreased casein, the major protein in milk. As most calcium in milk is associated with casein, the disruption of casein synthesis contributes to lowered calcium content in milk. The milk protein also continues to undergo further deterioration during processing and storage.

Mastitis occurs when white blood cells (leucocytes), are released into the mammary gland, usually in response an invasion of bacteria of the teat canal. Milk-secreting tissue, and various ducts throughout the mammary gland are damaged due to toxins by the bacteria. Bacteria that are known to cause mastitis include various *Staphylococcus*, *Mycoplasma*, and *Klebsiella* species. Mastitis is most often transmitted by contact with the milking machine, and through contaminated hands or materials.

BRIEF DESCRIPTION OF THE DISCLOSURE

The present disclosure relates to the use of halo active aromatic sulfonamide compounds as the active ingredient for cleaning the teats of bovines and other dairy animals. The teats of dairy animals are exposed to and carry bacteria which must be removed or neutralized prior to the milking process. Halo active aromatic sulfonamide compounds, such as chloramine-T, can be used for this sanitization process. It is particularly beneficial for controlling mastitis in dairy animals, but is not limited to the same.

Disclosed in embodiments is a process for sanitizing the teat area of a dairy animal, comprising applying an effective amount of a halo active aromatic sulfonamide compound to the teat area of the dairy animal.

Also disclosed in embodiments is a process for sanitizing the milking equipment for a dairy animal, comprising applying an effective amount of a halo active aromatic sulfonamide compound to the milking equipment. Many different pieces of milking equipment are discussed herein, and each piece can be cleaned with the halo active aromatic sulfonamide compound.

In some embodiments, the halo active aromatic sulfonamide compound has the structure of Formula (I):

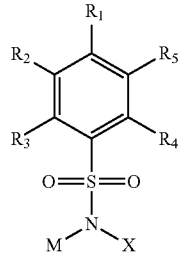

Formula (I)

wherein X is a halogen;

$R_1$, $R_2$, and $R_5$ are independently COOH, $NO_2$, $SO_3H$, COOM, a halogen, hydrogen, or a straight or branched aliphatic moiety from $C_1$ to $C_{12}$;

$R_3$ and $R_4$ are COOH, $NO_2$, $SO_3H$, COOM, a halogen, hydrogen, or a straight or branched aliphatic moiety from $C_1$ to $C_{12}$, except that an aliphatic moiety may not contain an alpha hydrogen;

wherein at least one of $R_1$, $R_2$, $R_3$, $R_4$, and $R_5$ is not hydrogen; and M is an alkali or alkaline earth metal.

In other embodiments, the halo active aromatic sulfonamide compound may have the structure of Formula (II):

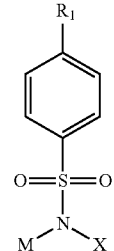

Formula (II)

wherein $R_1$ is COOH, $NO_2$, $SO_3H$, COOM, a halogen, or a straight or branched aliphatic moiety from $C_1$ to $C_{12}$;

X is chlorine, fluorine, bromine, or iodine; and

M is an alkali or alkaline earth metal.

In particular embodiments, $R_1$ is COOH or COOM.

Alternatively, the halo active aromatic sulfonamide compound can have the structure of Formula (III):

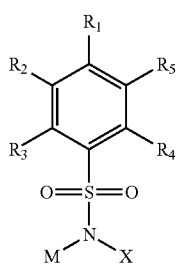

Formula (III)

wherein $R_1$, $R_2$, $R_3$, $R_4$, and $R_5$ are independently selected from hydrogen, COOR', CON(R")$_2$, alkoxy, CN, NO$_2$, SO$_3$R", halogen, substituted or unsubstituted phenyl, sulfonamide, halosulfonamide, and substituted or unsubstituted $C_1$-$C_{12}$ alkyl, wherein at least one of $R_1$, $R_2$, $R_3$, $R_4$, and $R_5$ is not hydrogen;

R' is hydrogen, an alkali metal, an alkaline earth metal, substituted $C_1$-$C_{12}$ alkyl, or unsubstituted $C_1$-$C_{12}$ alkyl;

R" is hydrogen or substituted or unsubstituted $C_1$-$C_{12}$ alkyl, where the two R" groups in CON(R")$_2$ may be independently selected;

X is halogen; and

M is an alkali or alkaline earth metal.

The halo active aromatic sulfonamide compound may be chloramine-T.

The halo active aromatic sulfonamide compound may be applied as a solution, particularly an aqueous solution.

The concentration of the halo active aromatic sulfonamide compound in the solution may be from about 0.0005 to about 5 weight percent, or in more specific embodiments from about 0.05 to about 1 weight percent.

The solution containing the halo active aromatic sulfonamide compound may include other additives. The solution may further comprise a coloring agent. The solution could further comprise a wetting agent. The concentration of the wetting agent in the solution can be from about 0.01 to 5 wt %. Alternatively, the solution may further comprise a skin conditioner. The concentration of the skin conditioner in the solution may be from about 0.1 to 5 wt %. The solution also might further comprise a thickening agent. The concentration of the thickening agent in the solution may be from about 0.1 to 5 wt %.

The solution may have a pH of from about 8 to about 9.5.

In particular embodiments, the solution consists of water, the halo active aromatic sulfonamide compound, an optional coloring agent, an optional wetting agent, an optional buffering agent, an optional skin conditioner, and an optional thickening agent.

In other embodiments, the solution consists of water, the halo active aromatic sulfonamide compound, a coloring agent, a wetting agent, a skin conditioner, and a thickening agent.

These and other non-limiting characteristics are more particularly described below.

DESCRIPTION OF THE PREFERRED EMBODIMENT

The modifier "about" used in connection with a quantity is inclusive of the stated value and has the meaning dictated by the context (for example, it includes at least the degree of error associated with the measurement of the particular quantity). In addition, the value or range endpoints so modified should also be considered as being disclosed. For example, the range "about 2 to about 4" should also be considered as disclosing the range "2 to 4".

Halo active aromatic sulfonamide organic compounds have been known and used for over one hundred years. Chloramine-T is an example of an old sulfonamide organic compound which has been used in many applications. The usefulness of Chloramine-T is predicated on its ability to release an active Cl+ ion when needed on demand, immediately after which, it simultaneously generates an active aromatic sulfo nitrene companion ion. The term "Cl+" refers to the fact that the chlorine atom has a +1 formal charge in a hypochlorite ion, ClO$^{-1}$, which is the form taken by the chlorine atom when dissociated from the sulfonamide compound. A chlorine atom is generally considered to have a charge of −1. Reference to the chlorine atom as having a +1 or −1 charge may be used in this application interchangeably because this terminology has no effect on the compound itself or its use. The active Cl+ ion and the companion aromatic sulfonitrene ion may work together to degrade or react with target molecules. This process makes the halo active aromatic sulfonamides useful in the odor control, biocidal and fungicidal arts.

The latent halogen ion released by halo active aromatic sulfonamide organic compounds, in accordance with this disclosure, is relatively covalent. This relative covalency assists to prevent the Cl+ ion from prematurely reacting and as such prevents the active molecule from having detrimental bleaching properties.

The new halo active aromatic sulfonamide compounds as used in this disclosure have excellent biocidal, fungicidal, and odor control properties. In addition many of these compounds have very low toxicity properties which make them attractive for usage as biocides, fungicides, or odor control agents in human, animal, and/or aquatic environments.

While any halo active aromatic sulfonamide is functional in accordance with this disclosure, chloro active sulfonamides are preferred.

The new halo active aromatic sulfonamide compounds which contain at least one halo active sulfonamide group, in accordance with this disclosure may have the structure of Formula (I):

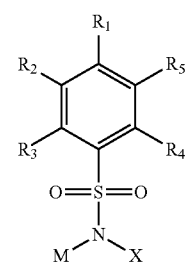

Formula (I)

wherein X is a halogen;

$R_1$, $R_2$, and $R_5$ are independently COOH, NO$_2$, SO$_3$H, COOM, a halogen, hydrogen, or a straight or branched aliphatic moiety from $C_1$ to $C_{12}$;

$R_3$ and $R_4$ are COOH, NO$_2$, SO$_3$H, COOM, a halogen, hydrogen, or a straight or branched aliphatic moiety from $C_1$ to $C_{12}$, except that an aliphatic moiety may not contain an alpha hydrogen;

wherein at least one of $R_1$, $R_2$, $R_3$, $R_4$, and $R_5$ is not hydrogen; and M is an alkali or alkaline earth metal.

The new halo active aromatic sulfonamide compounds which contain at least one halo active sulfonamide group may alternatively have the structure of Formula (II):

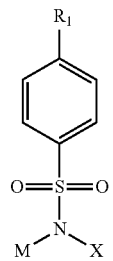

Formula (II)

wherein $R_1$ is COOH, $NO_2$, $SO_3H$, COOM, a halogen, or a straight or branched aliphatic moiety from $C_1$ to $C_{12}$;
X is chlorine, fluorine, bromine, or iodine; and
M is an alkali or alkaline earth metal.

The new halo active aromatic sulfonamide compounds which contain at least one halo active sulfonamide group may alternatively have the structure of Formula (III):

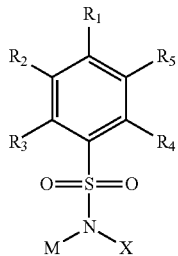

Formula (III)

wherein $R_1$, $R_2$, $R_3$, $R_4$, and $R_5$ are independently selected from hydrogen, COOR', $CON(R'')_2$, alkoxy, CN, $NO_2$, $SO_3R''$, halogen, substituted or unsubstituted phenyl, sulfonamide, halosulfonamide, and substituted or unsubstituted $C_1$-$C_{12}$ alkyl, wherein at least one of $R_1$, $R_2$, $R_3$, $R_4$, and $R_5$ is not hydrogen;
R' is hydrogen, an alkali metal, an alkaline earth metal, substituted $C_1$-$C_{12}$ alkyl, or unsubstituted $C_1$-$C_{12}$ alkyl;
R'' is hydrogen or substituted or unsubstituted $C_1$-$C_{12}$ alkyl, where the two R'' groups in $CON(R'')_2$ may be independently selected;
X is halogen; and
M is an alkali or alkaline earth metal.

Compounds of Formulas (I) to (III) may or may not be hydrated (n $H_2O$), but are generally isolated as a trihydrate where (n=3).

In specific embodiments of Formulas (I) to (III), M is sodium or potassium; and X is chlorine, bromine, or iodine. In other specific embodiments of Formulas (I) to (III), $R_1$ is COON, COOM, methoxy, or nitro.

The compounds of Formulas (I) to (III) are very stable and in particular they do not decompose in aqueous solutions. This property allows for easy compounding, long shelf lives, and allows high percentages of the compounds to be formulated into useful solution products.

Further the compounds of Formulas (I) to (III) have minimal bleach odor. This property is highly advantageous because formulations with a strong bleach odor are undesirable in most applications.

The activity of the aromatic chlorosulfonamido group of the compounds of Formulas (I) to (III) is regulated by the selection of specific R groups. R groups adjacent to the chlorosulfonamido group ($R_3$ and $R_4$) can cause steric effects and therefore change activity and/or cause stability changes on the chlorosulfonamido group. In addition, the various R groups can be effected differently. Specific increases or decreases in activity and stability may be noted. The usefulness of specific aromatic chlorosulfonamido groups may be affected by their different and unique inductive or resonance effects.

As is discussed above the compounds discussed herein are useful in a wide variety of arts. These arts include odor control, bacteria control, fungus control, soap formulations, paint formulations, the dairy cleansing art, stain removal and the aquatic disease control arts.

In accordance with the above discussion, one use of the compounds of this disclosure is for controlling odors in household, institutional and industrial applications. Perfumed odor control compositions do not destroy the odorous materials, but instead they only mask the odors caused by these materials. In contrast to this masking of the troublesome odorous material in the prior art, the sulfonamide compounds and processes of this disclosure react with the odorous molecules. In the prior art odor control compositions are perfumes wherein the odors are masked with synthetic or natural essence. In the present disclosure, instead of masking the odor with a perfume, the odor causing molecules are degraded by reaction with a Cl+ moiety and with the chemical moiety which remains after the Cl+ moiety is removed from the new sulfonamide compounds of this disclosure. The use of Cl+ is common in odor control, the most common Cl+ producing composition is household bleach. The preferred source of a Cl+ moiety for use in accordance with this invention are the new compounds as are represented by Formulas (I) to (III), as set forth above.

Bleach is commonly used as a source of Cl+ cations which are useful as deodorizers. Because of the problems associated with the use of bleach, i.e. the discoloration of the substrate, heavy, non discrete and detrimental oxidizing power, it is generally not suitable for use as a deodorizer. In addition the Cl+ cation which is produced by bleach is much more ionic and non discrete in its reactions when compared to the Cl+ cation produced by the compounds of Formulas (I) to (III). When compared to the Cl+ cation produced by bleach, the Cl+ cation produced by the compounds of Formulas (I) to (III) is much more covalent and less ionic and therefore is very selective in its reactions as a deodorizer, in other words the Cl+ cation attacks the odor source and not the substrate. As a result of this covalence, the side effects produced by the Cl+ cation produced by the compounds of Formulas (I) to (III) are not as severe as those produced by bleach. Therefore the Cl+ cation produced by the compounds of Formulas (I) to (III) can be used to deodorize as they do not have side effects such as strong bleach smell, the undesirable bleaching of the odor containing substrate etc. Further the compounds of Formulas (I) to (III) are more stable than bleach and have a higher Cl+ activity as compared to the Cl+ cation produced by bleach.

When compared to bleach, the compounds of Formulas (I) to (III) are a superior deodorizing agent because they are more selective and more covalent. Furthermore, the backbone remaining after the Cl+ cation is released from the compounds of Formulas (I) to (III) also reacts with the odor containing molecule thereby permanently removing it as a potential source of odor. In contrast, the chemical moiety which remains after the Cl+ cation is removed from bleach (i.e. the Na ion) has no ability to react with odor causing molecules.

Most odor causing molecules are mercaptans, sulfides heterocyclic or amine based compounds. The compounds of Formulas (I) to (III) are excellent agents for eliminating odors from these classes of compounds as both the Cl+ cation produced by the compounds of Formulas (I) to (III) and the residual chemical moiety remaining after the Cl+ cation is produced react with the odor causing molecules.

The halo active aromatic sulfonamide compounds of Formulas (I) to (III) can also be useful in accomplishing the desired goal of a sanitary milking operation. In addition, they can also reduce the incidence of mastitis in the bovine/dairy animal. The cleaning solutions contemplated by the present disclosure can reduce these problems when applied prior to and/or after milking, either to the teat of the bovine/dairy animal or to the associated milking equipment used to milk the dairy animal.

It is preferred that the concentration of the halo active aromatic sulfonamide compound in the cleaning solution be from about 0.0005 to about 5 wt %. The concentration of the active ingredient can also be from about 0.005 to about 1.0 wt %, with a more preferred range being from about 0.05 to about 1.0% weight percent, with the most preferred concentration being 0.75 wt % of the solution. These lower concentrations keep the bleach-like smell to a minimum but still give the desired odor control.

The halo active aromatic sulfonamide compounds are typically packaged in dry solid form. They can be dissolved in aqueous solution and used as a teat dip, spray, or the like on diary animals such as cows, goats, sheep, yaks, water buffaloes, horses, reindeer, and camels. Certain additives can be desirably included with the compounds, and as a result the finished commercial product may include one or two pouches, depending on whether the additives can be packaged dry or need to be in liquid form. Two specific embodiments are contemplated. In one embodiment, two dry pouches are used, with one dry pouch containing the halo active aromatic sulfonamide compound and the other dry pouch containing additives. In the other embodiment, one dry pouch is used and one liquid pouch is used.

Those additives can include coloring agents, wetting agents/surfactants, buffering agents, skin conditioners, thickening agents, and other additives. The resulting cleaning solutions effectively and quickly act to clean and sanitize the teat area, aiding the milking process and providing bacteria-free milk.

A coloring agent can be added to identify and confirm which teats have been cleaned using the cleaning solutions of the present disclosure. Suitable coloring agents include water soluble dyes, such as Graphtol Blue dye. The concentration of coloring agent in the solution is generally from about 0.5 to about 1.5 wt % of the solution.

In order for the halo active aromatic sulfonamide compounds of Formulas (I) to (III) to be effective they must come into contact with the bacteria on the surface of the teat. Beading can occur when the water portion of the solution evaporates, which reduces the surface area upon which the compounds are deposited. Thus, in some embodiments, a wetting agent or surfactant is added to the solutions of this disclosure to reduce the surface tension of the solution. As is discussed above the halo active aromatic sulfonamide compound functions in part by the reaction of the Cl+ moiety and the aromatic sulfonitrene ion with the bacteria. One aspect of this disclosure is concerned with the fact that many substances which are suitable for reducing the surface tension of the solution may adversely affect the formation of the Cl+ moiety from the halo active aromatic sulfonamide compound, or degrade said Cl+ moiety once it is formed.

Suitable substances which are useful for reducing the surface tension of the cleaning solutions of this disclosure are synthetic and natural wetting agents. Wetting agents are generally classified as cationic, anionic, amphoteric and nonionic. Because there are thousands of natural and synthetic wetting agents it is impossible to make generalizations as to which wetting agent would be effective in the composition of this disclosure. With this caveat it can be said that generally the most preferred wetting agents for use with the cleaning solution are anionic wetting agents, with the next preferred class of wetting agents being a nonionic wetting agents.

Amphoteric and cationic wetting agents are least preferred for use with the wetting agent embodiment of this disclosure.

Regardless of the above comments satisfactory agents may be found in any class of wetting agents.

While the applicant is aware of the vast range of wetting agents available, the applicant is not sure of all ramifications of how different wetting agents degrade the Cl+ moiety. It is felt that functional groups such as alkenes, alcohol, ketone, especially aliphatic ketones or aldehydes containing at least one alpha hydrogen next to the carbonyl carbon, and phenols as may be contained on the base wetting agent molecule are particularly harmful to the Cl+ moiety. Further while it is impossible for the applicant to explore all the ramifications thereof, impurities as may be contained in various commercially available wetting agents can play a significant part in the degradation of the Cl+ moiety. Impurities which are known to facilitate the degradation of the Cl+ moiety are aromatic and conjugated phenols, compounds containing activated carbonyl, alpha aliphatic hydrogen's or active primary and secondary amines.

The concentration of the wetting agent used in the cleaning solutions of this disclosure can be from about 0.01 to 5 wt % of the solution, including from about 0.1 to about 5 wt %. A more preferred concentration for the wetting agent is from about 0.5 to about 1.5 wt %. In order to achieve maximum efficiency, the surface tension of the solution must be reduced, so that the compounds of Formulas (I) to (III) can reach and react with the bacteria. An exemplary surfactant is Calsoft® F-90, which is a sodium dodecylbenzenesulfonate. An exemplary anionic wetting agent is sold under the trademark Avanel S-74 by the BASF Chemical Co. of Mt. Olive, N.J. The applicant believes that Avanel S-74 is sulfate capped alkyl ethoxylate, where the wetting agent contains 3 units of ethoxylate and the alkyl is a $C_8$ alkyl.

A factor in choosing the concentration of the wetting agent is the degree to which it foams. If undesirable foaming occurs anti foamers may be added to the solution.

For stability and for optimum performance the pH of a solution of the compounds of Formulas (I) to (III) should be between 6-14, with a more preferred pH range being between 8-9.5 with a most preferred range being between 8.5-9. Below a pH of 6 the compounds of Formulas (I) to (III) tend to decompose due to the acidic nature of the medium. While the solutions of this disclosure are effective above a pH of 10.0, solutions having a pH of above 10.0 can only be used for industrial applications, due to their caustic nature.

Aromatic N-Halo active sulfonamide solutions for use in this disclosure exhibit excellent stability at a pH range of 8-9.5. This stability is important in the domestic applications of this disclosure where long shelf life is very desirable.

Thus, the cleaning solution may in some embodiments include a buffering agent. Buffering agents which are suitable for use in accordance with this disclosure are sodium bicarbonate, potassium bicarbonate, sodium carbonate, potassium carbonate, acetate buffers (such as sodium acetate), phosphate buffers (such as tri and di sodium phosphate and mixtures thereof, pH blended phosphates, sulfate buffers (such as di and tri sodium sulfate and mixtures thereof.

Because of price, ease of use, low toxicity and their effect on the environment, the above listed sodium and potassium bicarbonates are preferred buffering agents for use in this disclosure. Buffered solutions are advantageous in that the active ingredients of the odor control solution of this disclosure can be shipped in powdered form and mixed by the consumer with no adverse effect.

The concentration of the buffering agent can be from 0.1 wt % up to the limit of solubility. The preferred range for the concentration of the buffering agent is from about 5 wt % to about 200 wt % of the active compound in solution. A more preferred range is from about 5 wt % to about 50 wt % with a most preferred concentration being 25-50 wt % of the solution.

The buffering of the solution compensates for any change in pH that may result from the conditions of application, the type of substrate, or industrial waste and the nature of the odor causing molecule.

Another additive which may be present in the cleaning solution is a skin conditioner. Skin conditioners generally reduce and promote the healing of any irritated skin on the teat which can arise from the milking machine or the environment, keeping the teat in good milking condition. Skin conditioners may include humectants (which promote moisture retention) and emollients (which soften the skin). Exemplary skin conditioners may include sorbitol, glycerin, mannitol, propylene glycol, and lanolin. The cleaning solution. The concentration of the skin conditioner used in the cleaning solutions of this disclosure can be from about 0.1 to 5 wt % of the solution.

A thickening agent may be used in the cleaning solution of the present disclosure. The thickening agent can be used to change the viscosity of the solution according to the desired mode of application. Exemplary thickening agents include hydroxyethyl cellulose, hydroxypropyl methyl cellulose, hydroxypropyl cellulose, methyl cellulose, carboxy methyl cellulose, emulsifying waxes, alkyl triammonium methosulfate, and ceteraryl octanoate. The concentration of the thickening agent used in the cleaning solutions of this disclosure can be from about 0.1 to 5 wt % of the solution.

It is at times desirable to have a very faint but highly attractive scent associated with its application. Therefore, the use of trace amounts of compatible perfume additives may be used in the formulations of the disclosure.

The cleaning solution can be initially sprayed or dipped on the teat prior to milking. The cleaning solution can be also be used as a post spray or post dip following milking.

In specific embodiments, the cleaning solution of the present disclosure consists of water, the halo active aromatic sulfonamide compound, an optional coloring agent, an optional wetting agent, an optional buffering agent, an optional skin conditioner, and an optional thickening agent.

In other specific embodiments, the cleaning solution consists of water, the halo active aromatic sulfonamide compound, a coloring agent, a wetting agent, a skin conditioner, and a thickening agent.

The cleaning solutions of the present disclosure can also be used to clean associated milking equipment. Several different pieces of equipment come into contact with the cow or the milk, and require cleaning and sanitizing to maintain the health of the dairy animal and produce sanitary milk. For example, milk can be hand drawn into a bucket. As another example, milking machines include several components. A cluster unit of the milking machine is used to milk each cow. Each cluster unit includes two or four teat cups (depending on the animal being milked). Each teat cup has a shell, a flexible liner, and a short pulse tube. The liner has a head, a barrel, and a short milk tube. The liner is the only part of the milking machine which is in direct contact with the teat. Liners are designed to provide an airtight joint at both ends of the shell, and to provide a mouthpiece and barrel which will fit on the teat to minimize liner slips and cluster fall off. It should milk fast, as complete as possible, and reduce teat congestion and injury. The teat cup uses a vacuum provided by the short pulse tube to provide a pulsating motion to the liner to stimulate milk flow from the teat into the short milk tube.

Each teat cup in the cluster unit is connected to a claw, which includes a long pulse tube and a long milk tube. The milk from each teat cup flows into the claw and into the long milk tube. The long pulse tube provides the vacuum to each teat cup.

The milk from the cluster unit flows through tubing to a milk receiver unit. Along the tubing, flow indicators and milk meters can be placed to gauge the milking rate and the quality of the milk produced by the individual dairy animal. If problems are found, then the milk can be discarded without contaminating milk collected from other animals. Because a large number of dairy animals are simultaneously being milked, a dairy operation usually has multiple milk receiver units. The milk is then sent from the milk receiver unit through a pipeline to a bulk tank, which collects the milk from several milk receiver units in one large tank.

It is contemplated that the cleaning solutions of the present disclosure that include the compounds of Formulas (I) to (III) can be used to clean the flexible liner, teat cup, milk tubes, tubing, milk receiver unit, flow indicator, milk meter, pipeline, bulk tank, the bucket, and generally any component which might contact the milk or be in close contact with the bovine/dairy animal. These individual components may be referred to herein as "milking equipment".

In some specific embodiments suitable for cleaning milking equipment, the cleaning solution of the present disclosure consists of water, the halo active aromatic sulfonamide compound, an optional wetting agent, and an optional buffering agent.

The compounds of Formulas (I) to (III) exhibit excellent biocidal activity against a wide variety of bacteria. This ability to kill bacteria lends the compounds of Formulas (I) to (III) to a wide variety of usages, for example as a bovine teat cleaner in the dairy arts etc.

For testing against *Staph* Epi, *E. coli*, VRE, MRSA, Pseudo., and Strep Gp A bacteria, an aqueous solution of 0.8 percent of a compound of Formula (II), with $R_1$ being COOH or COOM, was prepared. The solution further incorporated 0.2 percent sodium biocarbonate and 0.1 percent of an anionic wetting agent sold under the trademark Avenel S-74 was prepared, all percentages being weight percentages. The compound of Formula (II) was tested against various bacteria.

In these tests, the test solutions were sprayed on the specified bacteria cultures. The results of the tests are as specified in Tables I-III. All results are raw count.

TABLE 1

| | Number of CFU's per plate | | | | | |
|---|---|---|---|---|---|---|
| | Staph Epi | E. coli | VRE | MRSA | Pseudo | Strep Gp A |
| Control | 3700 | 480 | 2200 | 3300 | 450 | 1900 |
| 10 min | 0 | 0 | 0 | 0 | 0 | 0 |
| 5 min | 0 | 0 | 0 | 0 | 0 | 0 |
| 1 min | 15 | 0 | 190 | 26 | 0 | 530 |

TABLE 1-continued

Number of CFU's per plate

|  | Staph Epi | E. coli | VRE | MRSA | Pseudo | Strep Gp A |
|---|---|---|---|---|---|---|
| 30 Sec | 420 | 0 | 410 | 290 | 0 | 590 |
| 5 Sec | 3400 | 63 | 1300 | 1100 | 202 | 770 |

TABLE 2

Percent Survival

|  | Staph Epi | E. coli | VRE | MRSA | Pseudo | Strep Gp A |
|---|---|---|---|---|---|---|
| 10 min | 0 | 0 | 0 | 0 | 0 | 0 |
| 5 min | 0 | 0 | 0 | 0 | 0 | 0 |
| 1 min | 0.4 | 0 | 8.6 | 0.8 | 0 | 27.9 |
| 30 Sec | 11.3 | 0 | 18.6 | 8.8 | 0 | 31.1 |
| 5 Sec | 91.9 | 13.1 | 59.1 | 33.3 | 44.9 | 40.5 |

TABLE 3

Percent Kill

|  | Staph Epi | E. coli | VRE | MRSA | Pseudo | Strep Gp A |
|---|---|---|---|---|---|---|
| 10 min | 100 | 100 | 100 | 100 | 100 | 100 |
| 5 min | 100 | 100 | 100 | 100 | 100 | 100 |
| 1 min | 99.6 | 100 | 91.4 | 99.2 | 100 | 72.1 |
| 30 Sec | 88.7 | 100 | 81.4 | 91.2 | 100 | 68.9 |
| 5 Sec | 81 | 86.9 | 40.9 | 66.7 | 55.1 | 59.5 |

The test protocol for the test of Tables I-III was as follows:
1. Dry 0.5 μls of a Macfarland suspension of a fresh bacterial growth onto a 22×22 glass cover slip.
2. Spray composition on cover slips.
3. Transfer cover slip to 5 ml of broth and shake for 10 seconds.
4. Using a 10 μl loop, streak the broth onto a blood agar plate.
5. Incubate 24 hours at 35° C.
6. Perform colony count.
7. All testing will be performed in duplicate.
8. The controls will be handled in the same manner as the test slide except the controls will not be sprayed with the composition of Formula (II).
9. Calculate the percentage kill for each time interval by dividing the testing count by the control count.

As can be seen from the data of Tables I-III, all bacterial activity ceased in five minutes, with all bacterial activity essentially being terminated in one minute.

The data of Tables I-III demonstrates that the compound of Formula (II) is an outstanding biocide. This ability to kill a wide variety of bacteria can be put to good use in a wide variety of applications.

While the new halo active aromatic sulfonamide compounds of Formulas (I) to (III) are extremely toxic for bacteria, this property would be of little advantage if these compounds were toxic for mammals. In this connection a single dose oral toxicity test was conducted on rats. A 1% solution of the compound of Formula (II) was administered to ten healthy male Wistar Albino rats. These rats were dosed orally at a dosage rate of 5000 mg/kg of body weight. The rats were not fed for a period of 16-20 hrs prior to dosage and water was freely available at all times. After dosage the rats were observed 3-4 hours post dosage and daily for 14 days thereafter. None of the rats exhibited toxicity or pharmacological effects. If less than one half of the animals die at a dose of 5000 mg/kg a substance is considered to be non toxic in accordance with 16 CFR 1500.3(C)(2)(i).

In accordance with this test the compound of Formula (II) is considered to be non toxic for mammals and hence it is safe to use the compound of Formula (II) as a biocide in proximity to humans.

Further the compounds of Formulas (I) to (III) have minimal long term effects on the environment as they degrade in one to thirty days when exposed to the atmosphere and/or sunlight. As a result of this property the compounds of Formulas (I) to (III) have no detrimental long term effects on the ecosystem. This property is practically important as the compounds of Formulas (I) to (III) do not have a chance to accumulate in mammals, bird or aquatic life. Likewise the degradation byproducts of the compounds of Formulas (I) to (III) are non toxic to wildlife.

If desired, the user of the cleaning solution can also wash his/her hands in the solution.

The present disclosure is illustrated by the following Examples.

Example 1

Two dry solids packages, noted here as pouches A and B, were added to water.

| Pouch A contained: | |
|---|---|
| Chloramine-T | 2.600 lbs |
| Pouch B contained: | |
| Surfactant - Calsoft F-90 | 0.110 lbs |
| Hydroxyethyl cellulose | 1.870 lbs |
| Sorbitol | 2.200 lbs |
| Graphtol Blue dye | 0.220 lbs |

The two dry pouches A and B were dissolved in 55 gallons (~459 lbs) of water for the final formulation. The finished teat cleaning solution can be used after mixing. The final teat cleaning solution was ~466 lbs, and the concentration of the chloramine-T was 0.55 wt %.

Example 2

The teat cleaning solution was provided as a liquid pouch A and a dry solids pouch B.

| Pouch A contained: | |
|---|---|
| Chloramine-T | 2.600 lbs |
| Five gallons water | 41.750 lbs |
| Pouch B contained: | |
| Surfactant - Calsoft F-90 | 0.110 lbs |
| Hydroxyethyl cellulose | 1.870 lbs |
| Sorbitol | 2.200 lbs |
| Graphtol Blue dye | 0.220 lbs |

The contents of Pouch A were added to 50 gallons of water. The contents of dry pouch B were then added for the final formulation. The finished teat cleaning solution can be used after mixing. The final teat cleaning solution was ~466 lbs, and the concentration of the chloramine-T was 0.55 wt %.

The above description and drawings are illustrative of modifications that can be made without departing from the present disclosure, the scope of which is to be limited only by the following claims.

What is claimed is:

1. A process for sanitizing the teat area of a dairy animal or milking equipment related thereto, comprising:
applying an effective amount of a halo active aromatic sulfonamide compound of Formula (II) to the teat area of the dairy animal or to the milking equipment:

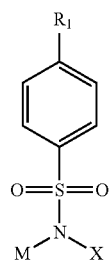

Formula (II)

wherein $R_1$ is COOH, $NO_2$ $SO_3H$, COOM, or a halogen;
X is chlorine, fluorine, bromine, or iodine; and
M is an alkali or alkaline earth metal.

2. The process of claim 1, wherein $R_1$ is COOH or COOM.

3. The process of claim 1, wherein the halo active aromatic sulfonamide compound is applied as a solution.

4. The process of claim 3, wherein the solution is an aqueous solution.

5. The process of claim 3, wherein the concentration of the halo active aromatic sulfonamide compound in the solution is from about 0.0005 to about 5 weight percent.

6. The process of claim 3, wherein the concentration of the halo active aromatic sulfonamide compound in the solution is from about 0.05 to about 1 weight percent.

7. The process of claim 3, wherein the solution further comprises a coloring agent.

8. The process of claim 3, wherein the solution further comprises a wetting agent.

9. The process of claim 7, wherein the concentration of the wetting agent in the solution is from about 0.01 to 5 wt %.

10. The process of claim 3, wherein the solution has a pH of from about 8 to about 9.5.

11. The process of claim 3, wherein the solution further comprises a skin conditioner.

12. The process of claim 11, wherein the skin conditioner is sorbitol, glycerin, mannitol, propylene glycol, or lanolin.

13. The process of claim 11, wherein the concentration of the skin conditioner in the solution is from about 0.1 to 5 wt %.

14. The process of claim 3, wherein the solution further comprises a thickening agent.

15. The process of claim 3, wherein the solution consists of water, the halo active aromatic sulfonamide compound, an optional coloring agent, an optional wetting agent, an optional buffering agent, an optional skin conditioner, and an optional thickening agent.

16. The process of claim 3, wherein the solution consists of water, the halo active aromatic sulfonamide compound, a coloring agent, a wetting agent, a skin conditioner, and a thickening agent.

* * * * *